United States Patent [19]

Linden et al.

[11] Patent Number: 5,854,081
[45] Date of Patent: Dec. 29, 1998

[54] STABLE EXPRESSION OF HUMAN $A_{2B}$ ADENOSINE RECEPTORS, AND ASSAYS EMPLOYING THE SAME

[75] Inventors: Joel Linden; Heidi Taylor; Anna Robeva, all of Charlottesville; Robin Woodard, Palmyra; Xiaowei Jin, Charlottesville, all of Va.

[73] Assignee: The University of Patent Foundation, Charlottesville, Va.

[21] Appl. No.: 670,175

[22] Filed: Jun. 20, 1996

[51] Int. Cl.[6] .................................................. G01N 33/566
[52] U.S. Cl. .......................... 436/501; 436/504; 435/69.1; 435/69.7; 435/320.1; 435/325; 530/350
[58] Field of Search .................................. 435/320.1, 325, 435/6, 69.1, 69.7, 172.1; 436/501, 504; 530/350

[56] References Cited

U.S. PATENT DOCUMENTS

| | | | |
|---|---|---|---|
| 5,426,048 | 6/1995 | Gearing | 435/252.3 |
| 5,462,872 | 10/1995 | Jonak et al. | 435/240.2 |
| 5,516,894 | 5/1996 | Reppert | 530/350 |
| 5,599,671 | 2/1997 | Jacobson et al. | 435/6 |

OTHER PUBLICATIONS

Robeva et al., Biochemical Pharmacology 51 (4):545–55 Feb. 23, 1996.
Zhao et al., Gene 137:345–6 1993.
Witzgall et al., Analytical Biochemistry 223:291–298 1994.
Nilsson et al., Journal of Molecular Recognition 9 (5–6):585–594 1996.

*Primary Examiner*—Lorraine Spector
*Assistant Examiner*—Eliane Lazar-Wesley
*Attorney, Agent, or Firm*—Oblon, Spivak, McClelland, Maier & Neustadt, P.C.

[57] ABSTRACT

Stable over-expression of native and hexahistidine/FLAG extended recombinant human adenosine receptors permits recovery of membranes and membrane fragments bearing a high density of adenosine receptors. Cell lines expressing all four sub-types of human adenosine receptors have been identified. The receptors, and membranes and membrane fragments bearing the same, can be used in assays to screen compounds for binding ability to the adenosine receptors, such as potential pharmaceutical agents.

7 Claims, 14 Drawing Sheets

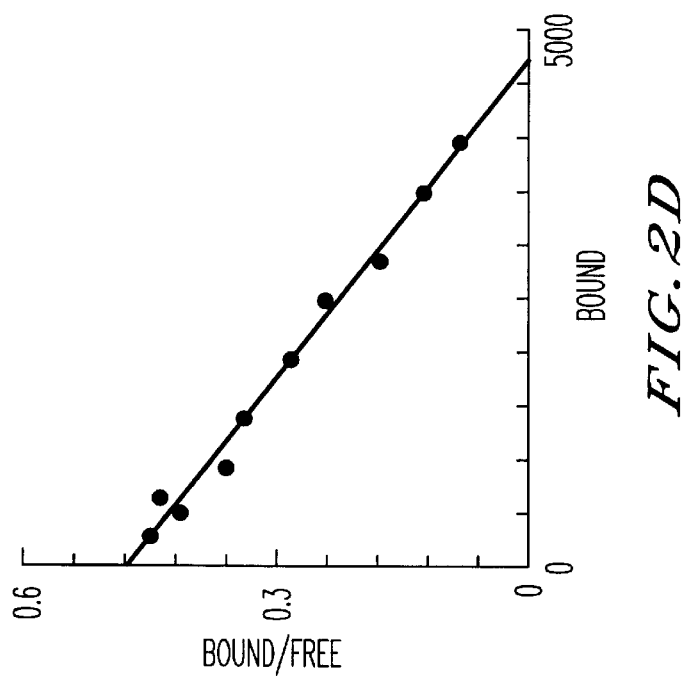
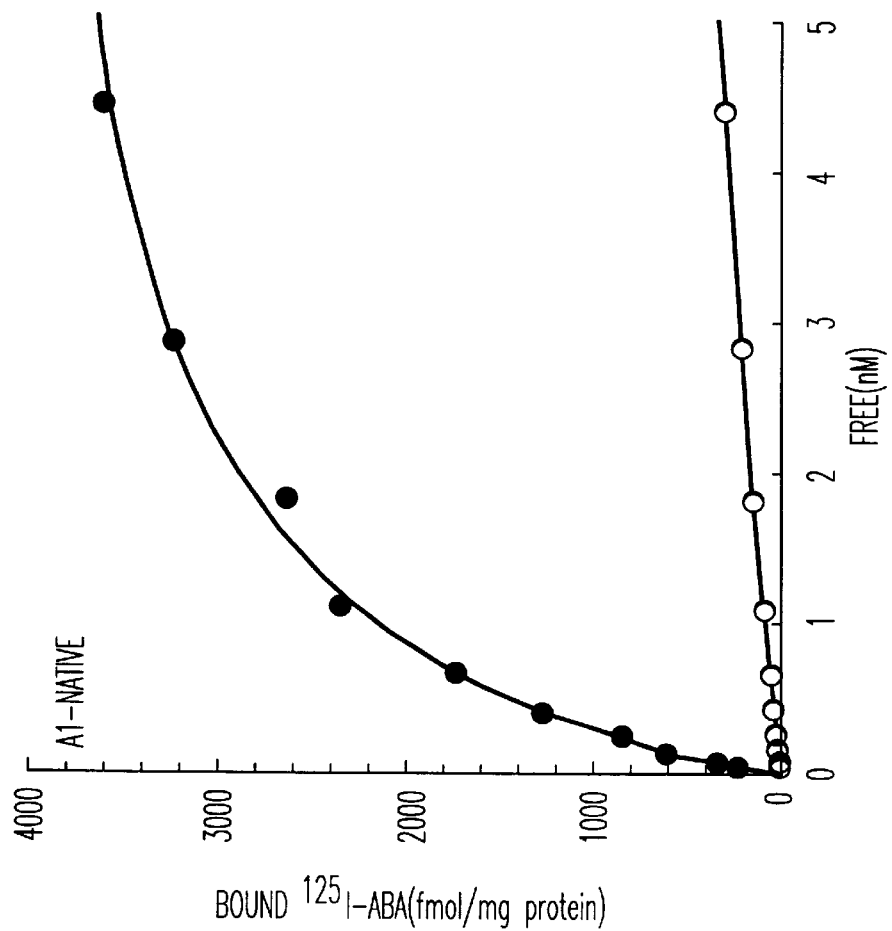

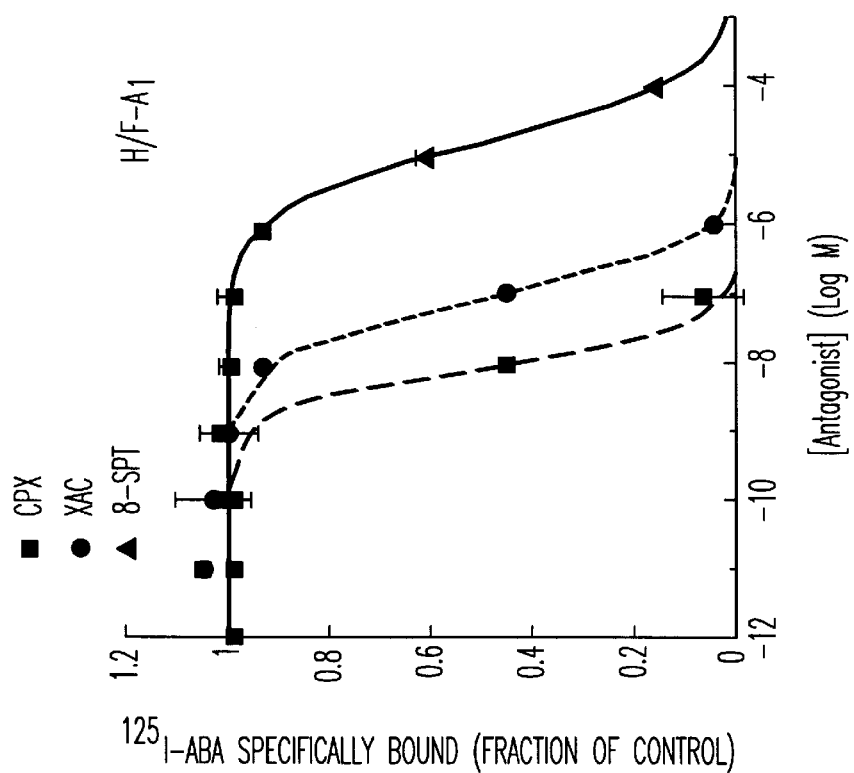
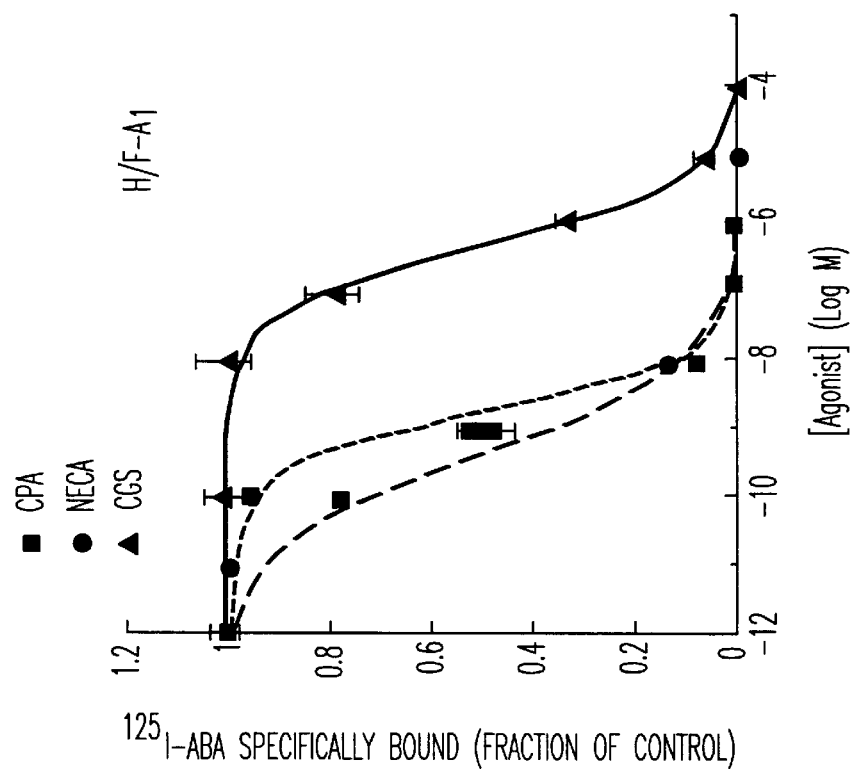
FIG. 4B
FIG. 4A

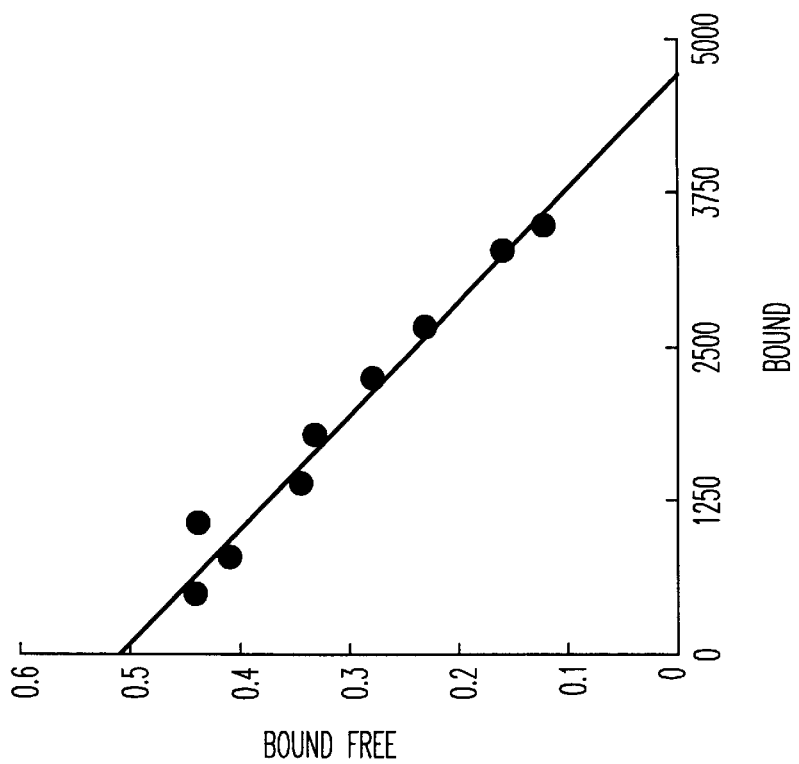
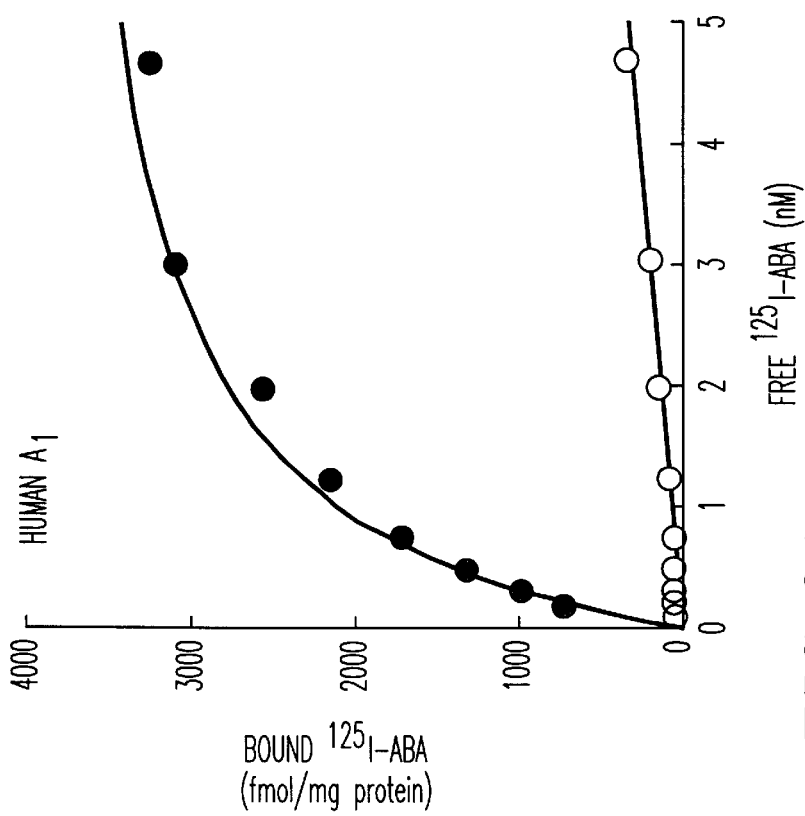
FIG. 6B
FIG. 6A

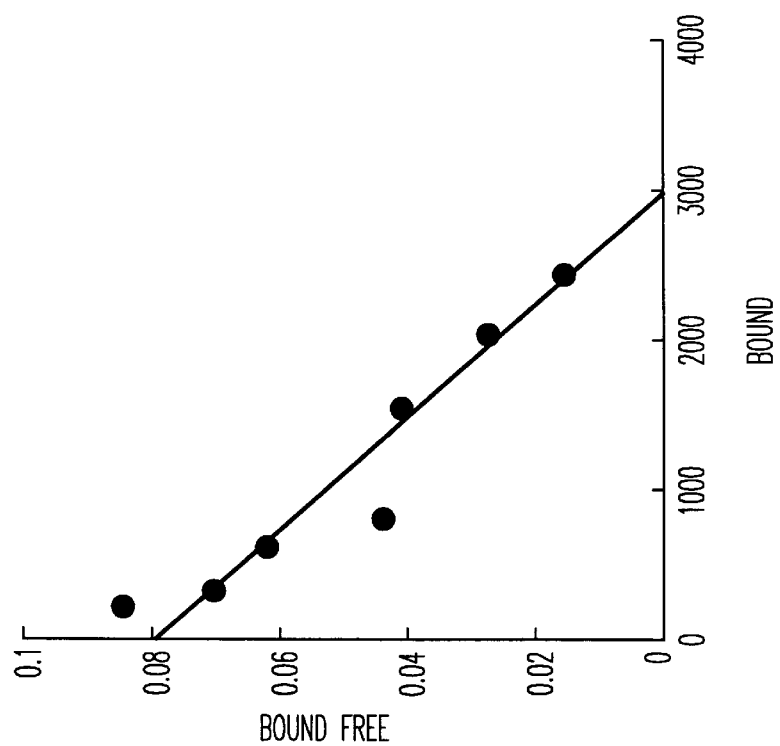
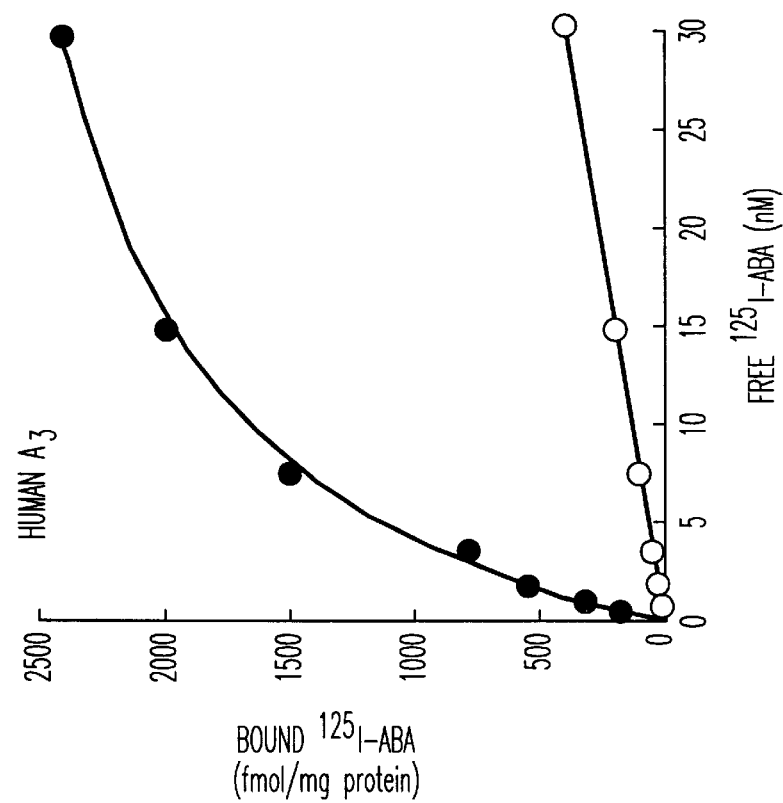
FIG. 6H
FIG. 6G

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp   Tyr   Lys   Asp   Asp   Asp   Asp   Lys
    1                                  5

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:2:

CGTCAAGCTT  AGATCTGAAT  TCGCGATGGC  ACACCATCAC  CATCACCATG  AC          52

( 2 ) INFORMATION FOR SEQ ID NO:3:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:3:

CAGGATCCAC GCGTTCTAGA CTTGTCATCG TCGTCCTTGT AGTCATGGTG ATG     53

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:4:

CCATATAGAA TGCCGCCCTC CATCTCAGC     29

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:5:

GCTACGCGTC TAGTCATCAG GCCTCTCTTC     30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:6:

CCATCTAGAA TGCCCATCAT GGGCTCCTCG     30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA PRIMER"

( x i ) SEQUENCE DESCRIPTION: SEQ ID NO:7:

GCTGGATCCT CAGGACACTC CTGCTCCATC     30

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

| Met | Ala | His | His | His | His | His | His | Asp | Tyr | Lys | Asp | Asp | Asp | Asp | Lys |
|---|---|---|---|---|---|---|---|---|---|---|---|---|---|---|---|
| 1 | | | | 5 | | | | | 10 | | | | | 15 | |

Ser Arg

STABLE EXPRESSION OF HUMAN A$_{2B}$ ADENOSINE RECEPTORS, AND ASSAYS EMPLOYING THE SAME

This invention was made in the course of work under Contract No. NIH R01-HC37942. The United States Government may have rights in this invention.

BACKGROUND OF THE INVENTION

1. Field of the Invention

This invention pertains to cells that stably over express recombinant human adenosine receptors. Specifically, cells have been prepared, and maintained, which stably express large amounts of all four types of human adenosine receptors. This invention also pertains to assays that can be used to screen compounds to determine their affinities for human adenosine receptors.

This invention also pertains to the construction of a vector (pDouble Trouble or pDT) that extends recombinant receptors on their amino terminal with extra sequences to facilitate receptor purification.

2. Background of the Prior Art

At least four human adenosine receptors have been identified, that are the subject of abundant study. Adenosine, a key metabolic nucleoside, frequently affects cellular reactions by interaction with membrane receptors. To intervene at a cellular level, in the treatment of a wide variety of conditions and disease states, it is desirable to be able to specifically block, or promote, adenosine interaction with a specific receptor, or receptor sub-type. Thus, information regarding receptors, the ability to test various adenosine receptors for response activity, and the availability of specific receptors to screen potential binding compounds, and the like, for both therapeutic and diagnostic purposes, is of particular importance.

Human adenosine receptors have been cloned by several groups. See, e.g., Libert et al., Biochem. Biophys. Res. Comm. 187:919–926 (1992); Furlong, et al., Mol. Brain Res. 15:62–66 (1992) and Pierce, et al., Biochem. Biophys. Res. Comm. 187:86–93 (1992). Indeed, Genebank Accession Numbers for all four human adenosine receptor subtypes are available.

A$_1$: L22214, S45235, S56143
A$_{2A}$: M97370, S46950
A$_{2B}$: M97749
A$_3$: L20463

Expression levels of these receptors have, however, been disappointing. The A$_1$ adenosine receptor was expressed at a level of 1.92 pmol/mg protein. Libert et al. While expression of the A$_{2A}$ receptor and radioligand ([$^3$H]CGS21680) binding has been reported, expression levels are not given. Suzuki et al., J. Med. Chem. 35:3066–3075 (1992). Expression levels for this receptor at concentration optimal for pharmaceutical screening has not been reported. The expression of recombinant human A$_3$ receptor was reported to a level of about 0.25 pmol/mg protein, Salvatore et al., Proc. Natl. Acad. Sci. USA 90:10365–10369 (1993) and while expression of the A$_{2B}$ receptor has been demonstrated by measuring cyclic AMP content, Pierce et al., as no binding assay has ever been reported for this receptor, the level of expression must be low indeed. In any event, the expression level could not be assessed. Thus, the expression levels, even for recombinant human adenosine receptors, have been quite low. Low expression levels hinders or precludes the use of these recombinant receptors to screen potential binding compounds, such as the potential therapeutic agents.

None of the attempts to clone various receptors have resulted in sufficient expression of adenosine receptors, or sufficient purification of the same, to allow the preparation of membranes with over expressed adenosine receptors thereon, or similarly, to conduct screening assays and the like employing specific adenosine receptors.

Accordingly, it remains an object of those of skill in the art to provide cells, or other sources, of over expression of all four types of human adenosine receptors, in a form that allows detection of receptor-adenosine binding, and the screening of potentially active compounds.

Receptors are low abundance membrane proteins that are notoriously difficult to purify.

SUMMARY OF THE INVENTION

The above objects, and others made clear by the discussion below, have been achieved the preparation of cells that stably express large amounts of all four types of human adenosine receptors. These cells provide membranes, which can be used to screen compounds to determine their affinities for human adenosine receptors. As such, they are potentially useful as screening materials for drug discovery. This utility has been demonstrated by radioligand binding, showing receptor subtype specificity for a variety of compounds. These recombinant receptors are modified by adding amino acids to facilitate purification. This is done by adding six adjacent histidines (hexahistidine) and adding the eight amino acid FLAG epitope. We have constructed a vector, pDouble Trouble that adds hexahistidine (H) and FLAG (F) to recombinant adhesive receptors. H/F-extended receptors can readily be purified.

DETAILED DESCRIPTION OF THE INVENTION

Abbreviations user herein include:

Ni-NTA=Ni-nitrilotriacetic acid

FLAG =Asp-Tyr-Lys-Asp-Asp-Asp-Asp-Lys (SEQ ID NO:1)

H/F=HIS6-FLAG

CPA=N$^6$-cyclopentyladenosine

NECA=5'-N-ethylcarboxamidondenosine

CGS21680=2-(r-(s-carboxyethyl)phen-ethylamino)-5'-N-ethylcarboxamidondenosine

XAC=xanthine amino congenen

8SPT =8-P-sulfophenyltheophylline

CPX=8-cyclopentyl-1,3-dipropylxanthine

PCR=polymerase chain reaction

1-ABOPX (BW-A522)=3-iodoaminobenzyl-1-propyl-8-p-(oxyacetate)-phenylxanthine

DMEM=Dulbecco's Modified Eagle's Medium

ABA=N'-aminobenzyladenosine

Az-BW-A844=8-cyclopenryl-3-azidophenethyl-1-propylxenthine pDT=pDouble Trouble (CLDN10B modified to contain hexahistidine, the FLAG peptide, and additional restriction sites)

Figure 1:
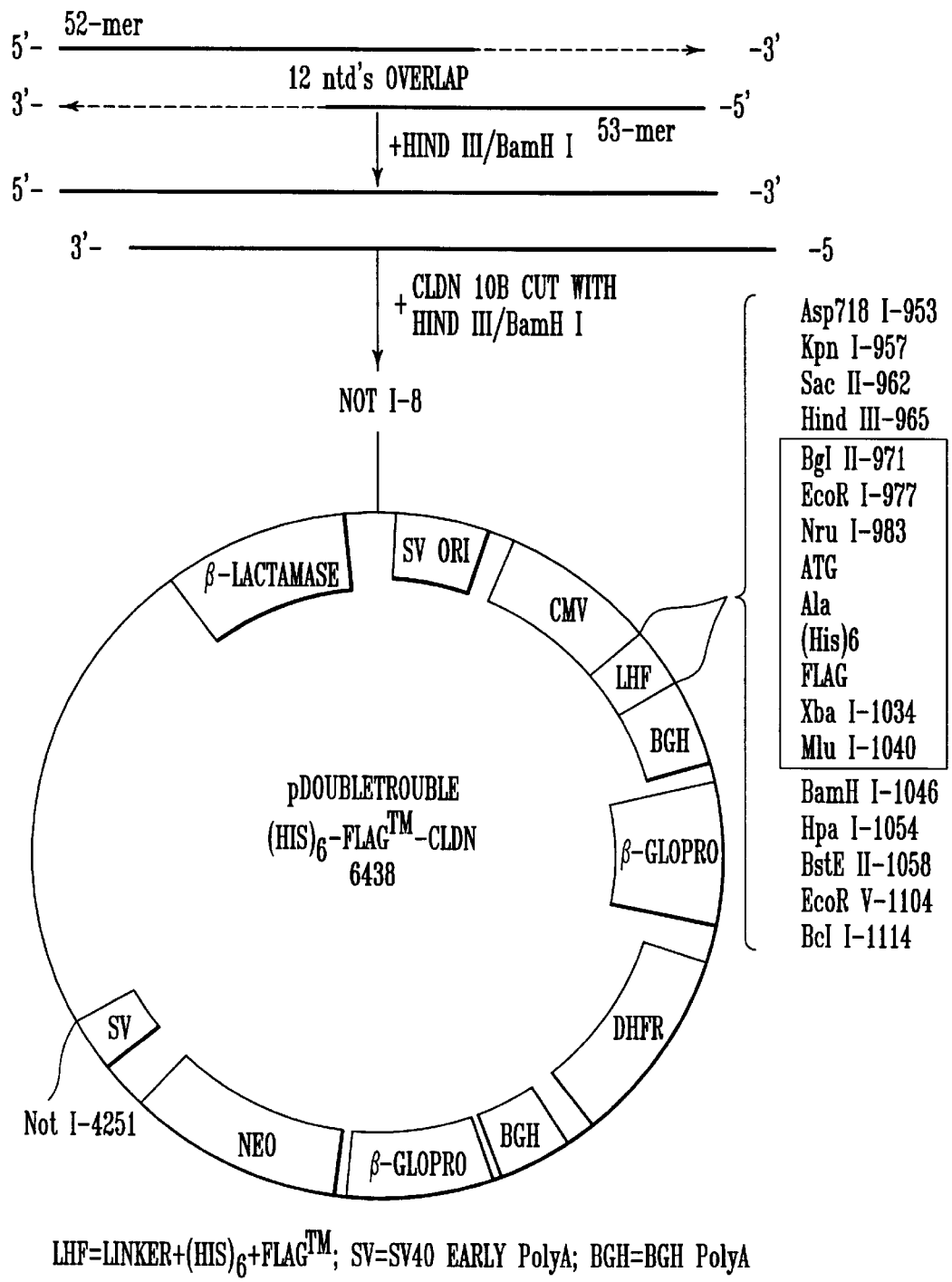
FIG. 1 is a descriptive schematic of the composition of the pDT expression vector used to express native or H/F-adenosine receptors.
Figure 2B:
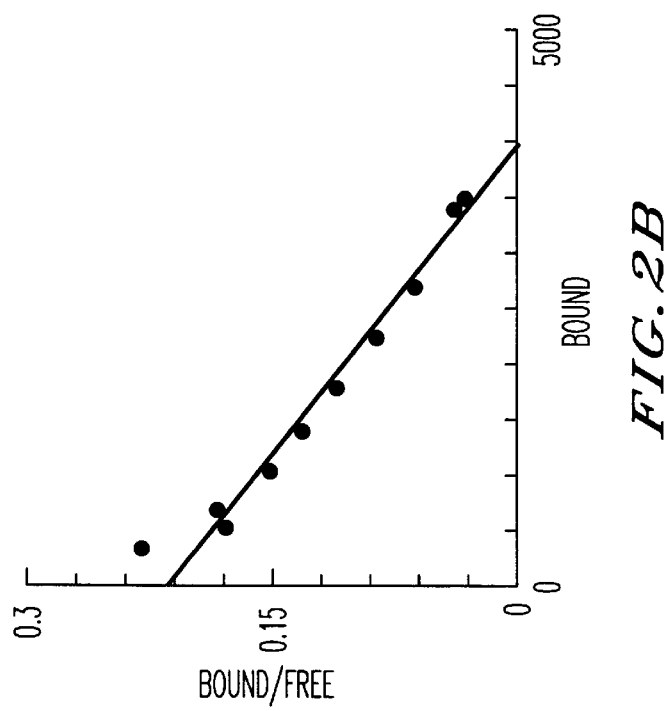
FIG. 2 comprises graphs reflecting equilibrium binding of radioligands to human recombinant wildtype and H/F A$_1$ adenosine receptors.
Figure 2A:
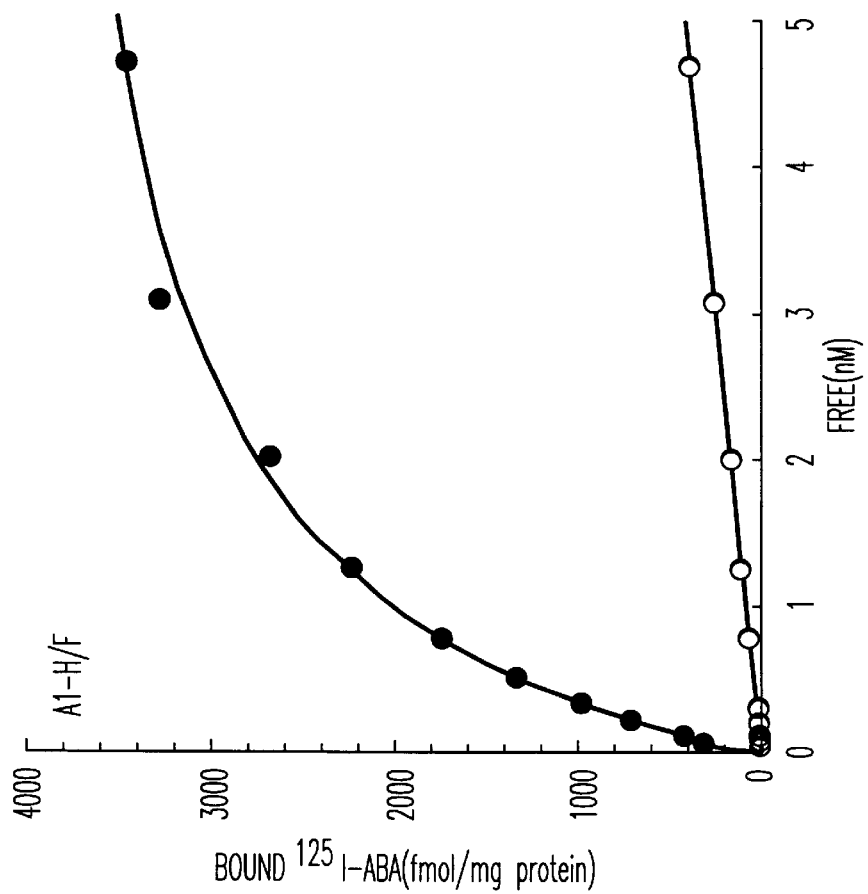
Figure 2F:
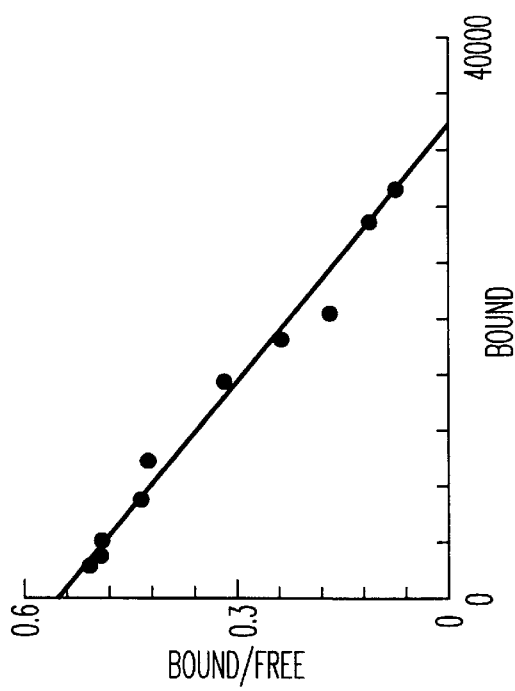
Figure 2E:
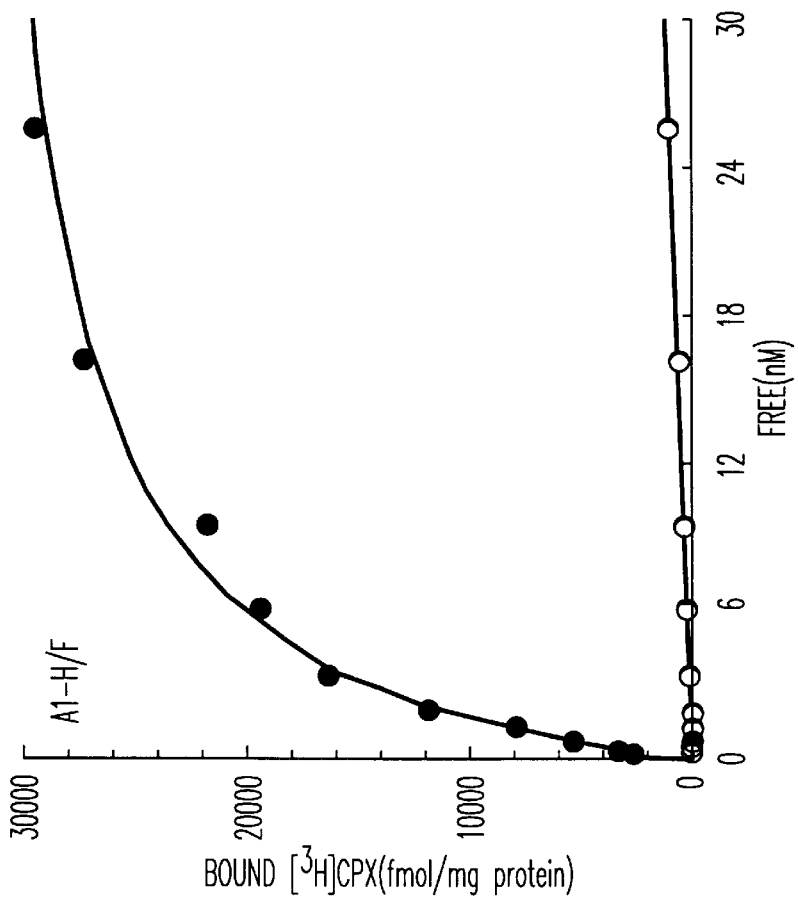
Figure 2H:
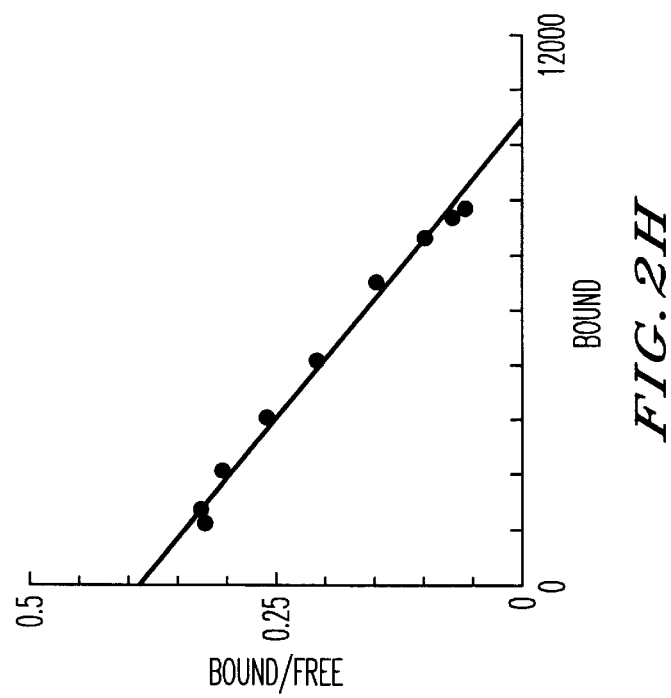
Figure 2G:
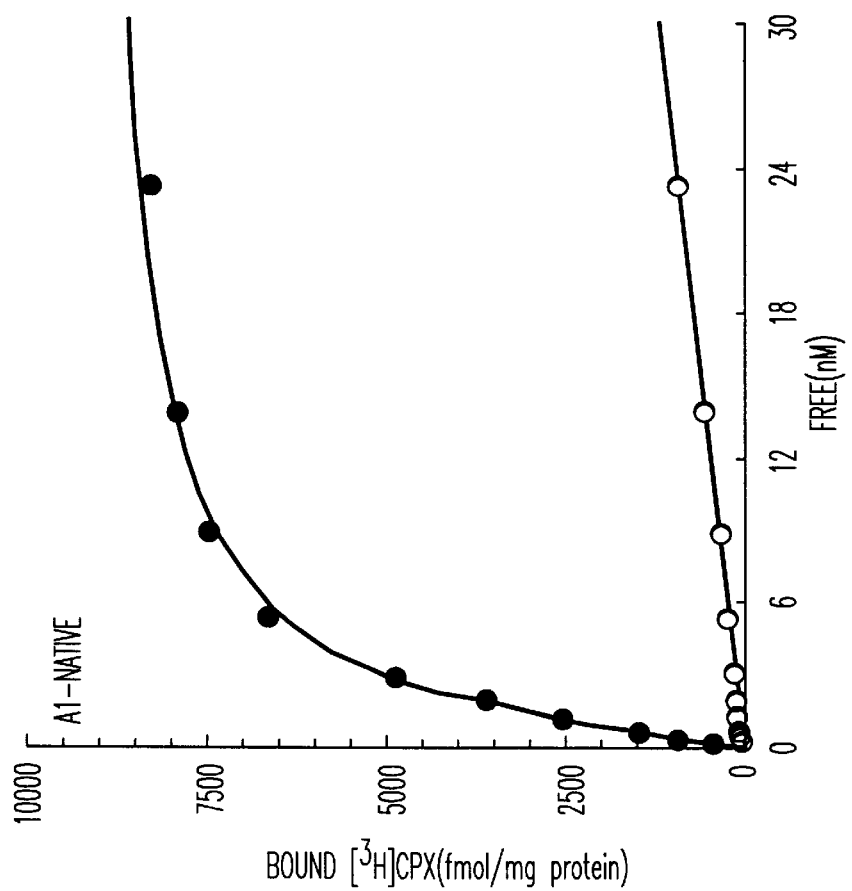
Figure 5:
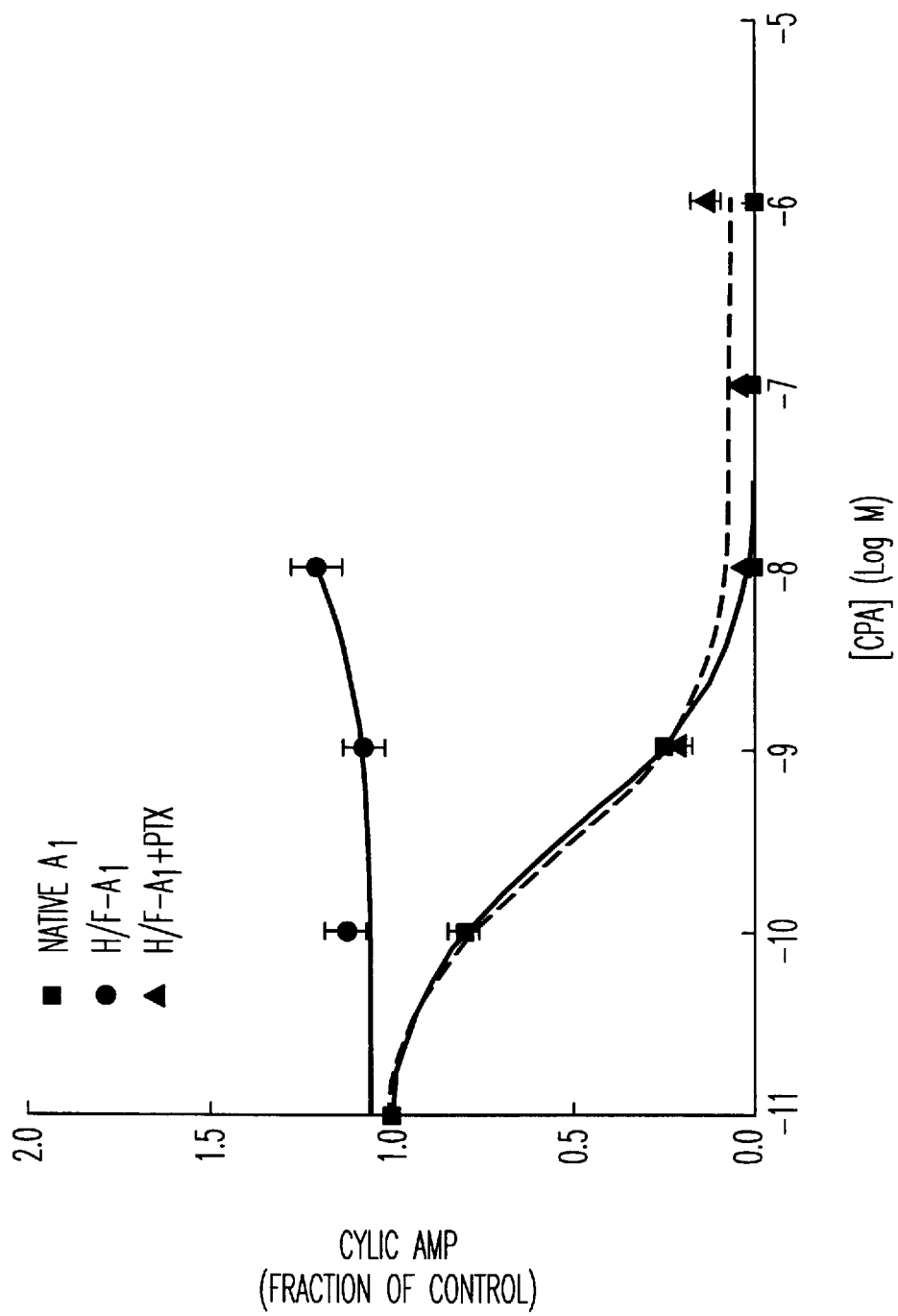
FIG. 5 demonstrates inhibition of function (cyclic AMP accumulation) in CHO-K1 cells expressing recombinant human native and H/F-A$_1$ adenosine receptors.

An expression plasmid for mammalian cells (CLDN10B) has been modified to add nucleotides encoding hexahistidine (H) and the FLAG peptide (F) to cDNAs. The new mammalian expression plasmid has been named pDoubleTrouble (pDT) (FIG. 1). The pDT plasmid and a recombinant baculovirus were used to produce native and H/F-human $A_1$ and $A_{2A}$-adenosine receptors, and subsequently human $A_{2b}$ and $A_3$ receptors optimally expressed in CHO-K1 and S19 cells, respectively. The cells are continuously available from the Health Sciences Center, University of Virginia, Charlottesville, Va. 22908. Binding to recombinant $A_1$-receptors ($B_{max}$=30 pmol/mg protein) was characterized using [$^3$H]8-cyclopentyl-1,3-dipropylxanthine. By comparison to the native receptors, the addition of H/F to the amino termini of these receptors had no effect on the binding affinities of radioligands or competing compounds (FIG. 2). The function of $A_1$ adenosine receptors to reduce forskolin-stimulated cyclic AMP accumulation in intact cells was not affected by the H/F extension (FIG. 5). Anti-FLAG and Ni-nitrilotriacetic acid affinity chromatography resulted in high yield (>50 percent overall recovery) of nearly homogeneous (>90 percent pure) receptors visible on silver-stained gels that co-migrated with photolabeled receptors before and after deglycosylation with N-glycosidase F. The purification of membrane proteins, such as G protein-coupled receptors, is difficult because of their high degree of purification required and the need for solubilization of proteins in detergent prior to their purification. The most successful strategy has been to adsorb receptors to immobilized ligands. For example, small amounts of $A_1$ adenosine receptor-G protein complexes have been purified to various degrees by ligand affinity to chromatography, Munshi et al, "J. Biol. Chem." 264:14853–59 (1989), Nakata, "J. Biol. Chem." 264:16545–51 (1989). Recombinant technology provides alternatives to ligand affinity chromatography for purifying large quantities of receptors in that: (1) more recombinant receptors can be expressed in cultured cells than are found in tissues; (ii) a homogeneous population of receptors can be expressed; and (iii) recombinant receptors can be modified to contain an extra sequence to facilitate purification.

One peptide sequence that has been widely added to recombinant proteins to facilitate protein purification is hexahistidine, which binds avidly to metal chelate affinity columns, such as Ni-NTA.

It has been found that recombinant $A_1$ adenosine receptors engineered to contain hexahistidine at either the amino or carboxyl terminus could be purified to 200- to 300-fold, not enough to effect purification to homogeneity. A second means of purifying recombinant proteins is to engineer in an antibody epitope. Numerous epitopes have been used. The FLAG system utilizes immobilized anti-FLAG antibodies to purify recombinant proteins containing the eight amino acid FLAG epitope (Asp-Try-Lys-Asp-Asp-Asp-Asp-Lys). The FLAG peptide can be cut after its C-terminal amino acid by enterokinase, and so removed from the amino terminus of purified proteins. The preparation of vectors designed to express receptors extended on the amino terminus with hexahistidine and the FLAG epitope is described herein. This extension has been added to human $A_1$, $A_{2A}$, $A_{2b}$, $A_3$ adenosine receptors and found not to alter ligand binding properties and to permit the purification of the H/F-$A_1$ and H/F-$A_{2A}$ receptors in high yield and to high purity. The degree of purification achieved by the one of both FLAG and hexahistidine markers, has not been achieved using prior art single tags. The receptors have been purified to homogeneity, based on silver staining of SDS polyacrylminate gels.

Figure 7:
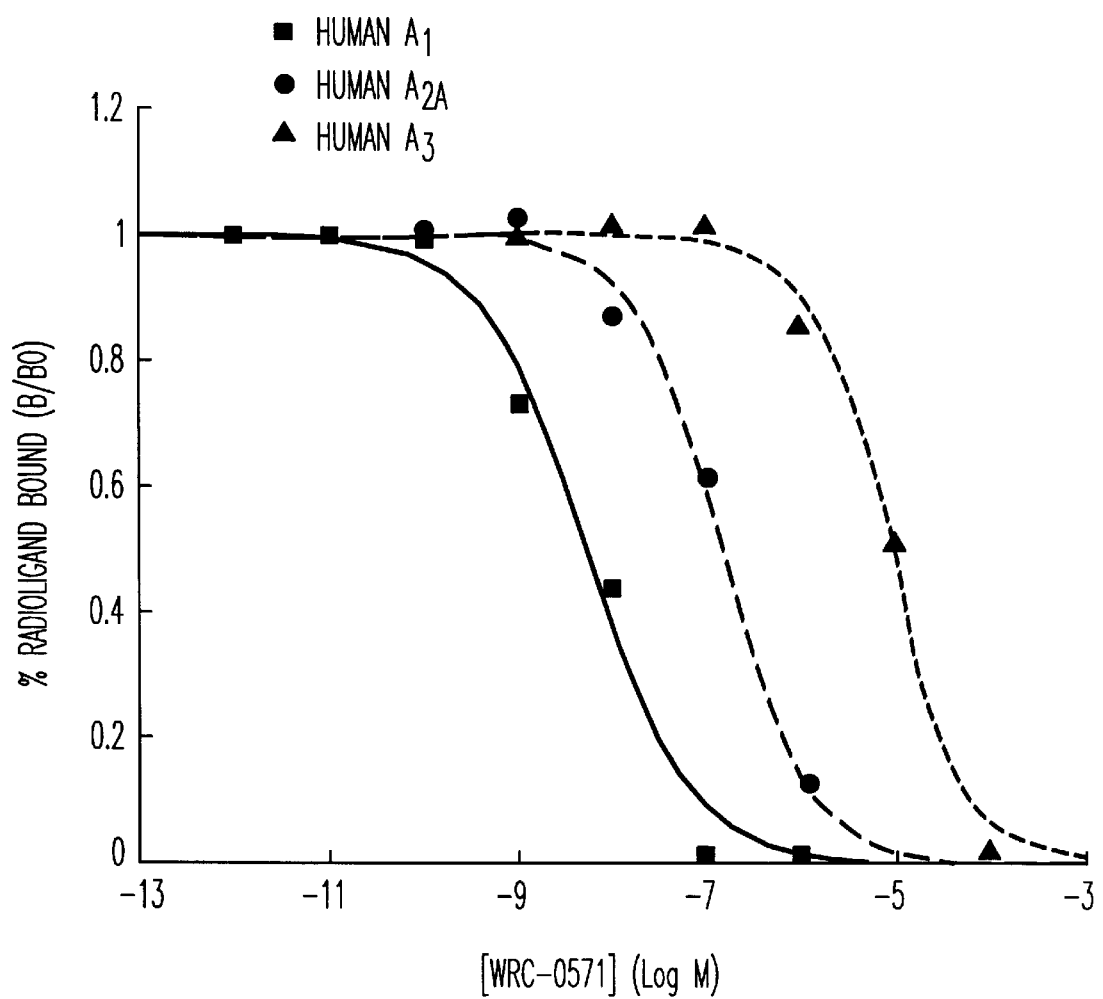
FIG. 7 demonstrates equilibrium binding of radioligands to recombinant native human adenosine receptors. Specific and non-specific binding are shown on the left, while Scathard plots are shown on the right.

In contrast to prior attempts at expression of these receptors, applicants have obtained high levels of expression of the recombinant receptor (FIG. 7). Thus, by the methods described in detail herein, the expression level for the $A_1$ receptor is about 30 pmol/mg protein. The expression level of the $A_{2A}$ human adenosine receptor obtained through this invention is extraordinarily high, about 50 pmol/mg protein. Expression of the $A_3$ receptor has been achieved at levels of about 5 pmol/mg protein, and even human adenosine receptor $A_{2B}$, from which there is no known binding assay in the prior art, has been expressed at levels adequate for potential drug screening and the like, about 5 pmol/mg protein.

MATERIALS AND METHODS

CPA, NECA, CGS21680, XAC and 8-SPT were purchased from Research Biochemicals, International (Natick, Mass.); CPX, I-ABOPX (BW-A522), ABA, and 1-ABA were gifts from Susan Daluge of Glaxo Wellcome (Research Triangle Park, N.C.); [$^3$H]CPX, [$^3$H]NECA, and [$^3$H] CGS21680 were from New England Nuclear (Boston, Mass.). To synthesize $^{125}$I-ABA, ABA was radioiodinated and purified with HPLC as described previously. cDNAs encoding human $A_1$ and $A_{2A}$ adenosine receptors were gifts of Marlene Jacobson (Merck & Co., West Point, Pa.). Identical cDNAs were identified following PCR of human brain cDNA (Clonetech, Palo Alto, Calif.). The oligonucleotides were used for construction of the hexahistidine/FLAG construct and PCR reactions were synthesized in the Biomolecular Research Facility of the University of Virginia. The expression vector, CLDN10B, was a gift from Mitch Reff (SK&F Laboratories, Philadelphia, Pa.).

Restriction enzymes, competent JM109 *Escherichia coli* and Wizard mini and megaprep DNA purification systems were purchased from the Promega Corp. (Madison, Wis.); vent DNA polymerase was from New England BioLabs, Inc. (Beverly, Mass.), and a sequence Version 2.0 DNA sequencing kit from United States Biochemical Corp. (Cleveland, Ohio). Adenosine deaminase and N-glycosidase F were obtained from Bochringer Mannheim Biochemicals (Indianapolis, Ind.); bacterial culture medium was from BIO 101, Inc. (LaJolla, Calif.); mammalian tissue culture medium and reagents were from Gibco BRL (Grand Island, N.Y.); pVL1392 and the linear wild-type AcMNPV viral DNA for baculovirus expression from Invitrogen (San diego, Calif.); and low melting point agarose and the reagents used for SDS electrophoresis from Bio-Rad Laboratories (Richmond, Calif.). SeaKeth LE agarose was obtained from FMC Bioproducts (Rockland, Me.); FLAG peptide and Anti-FLAG M2 Affinity Gel were from Kodak IBI (New Haven, Conn.); and digitonin was from Gallard-Schlesinger Industry, Inc. (Carle Place, N.Y.). All other reagents were purchased from the Sigma Chemical Co. (St. Louis, Mo.).

CONSTRUCTION OF HIS$_6$-FLAG-CLDN10B (pDOUBLETROUBLE) EXPRESSION VECTOR:

To construct an oligonucleotide that encodes hexahistidine-FLAG to be inserted into CLDN10B, two synthetic oligonucleotides (52-mer forward: 5'-CGTCAAGCTTAGATCTGAATTCGCGATGGCACA CCATCA-CCATCACCATGAC-3' and 53-mer reverse: 5' C A G G A T C C A C G C G T T C T A G A C T T G T C - ATCGTCGTCCTTGTAGTCATGGTGATG-3') bearing Hind III and Bam H1 restriction endonuclease sites at their 5' ends and 12 complementary nucleotides at their 3' ends, were annealed in a 1:1 molar ratio (60 pmol) each at ambient temperature for 15 minutes (SEQ ID. NO:2–3). The primers were extended to generate a 93 bp DNA fragment by the action of the Klenow fragment of DNA polymerase I. To make the expression plasmid, pDT, (FIG. 1) the H/F DNA product and the CLDN10B expression vector were digested with Hind III/Bam H1 restriction enzymes, purified by low melting point agarose gel electrophoresis (1.7 percent agarose, 1 µg/mL ethidium bromide in 1×Tris borate EDTA) and in-gel ligated at 16° using T4 DNA ligase. After transfection of E. coli JM109, several ampicillin resistant colonies were isolated, purified by Wizard miniprep DNA purification, and screened for positive recombinants by restriction digestion with Stu 1 (a unique restriction site for the parent CLDN10B vector) in combinations with each of BGl II, Nru I and Mlu I restriction enzymes, introduced by the PCR fragments. The sequence of the 93 bp fragment was confirmed by Sanger's dideoxynucleoside chain termination method using CLDN10B specific primers.

This expression vector, a plasmid comprising nucleotide sequences for hexahistidine and FLAG upstream of the structural genetic sequence protein, can be used to provide for recombinant expression of any protein difficult to purify through conventional means.

CLONING OF HUMAN $A_1$ and $A_{2a}$ ADENOSINE RECEPTOR cDNAs INTO pDT AND BACULOVIRUS EXPRESSION VECTORS:

PCR was used to introduce Xba IMlu I restriction sites to human $A_1$ and Xba I IBam $H_1$ restriction sites to human $A_{2A}$ adenosine receptor cDNAs upstream of the native ATG initiation codon and downstream of the native stop codon, respectively. Two oligonucleotides for $A_1$ (forward: 5'-CCATATAGAATGCCGCCCTCCATCTCAGC-3' and reverse: 5'-GCTACGCGTCTAGTCATCAGGCCTC TCTTC-3') and two oligonucleotides for $A_{2A}$ (forward: 5'-CCATCTAGAATGCCCATCAT-GGGCTCCTCG-3', and reverse: 5'-GCTGGATCCTCAGGACACTCCTGC TCCATC-3') were designed with their 3'ends corresponding to the first 20/21 nucleotides of the 5' or 3' ends of the coding region of human $A_1$ and $A_{2A}$ adenosine receptor cDNAs (SEQ ID NO:4–7). The flanking oligonucleotide sequences include restriction sites and some extra nucleotides to facilitate restriction digestion near the ends of the resulting PCR products. PCR reactions were carried out in a volume of 50 µL, 17–20 pmol of each primer, 0.25 mM dNTPs and 2 U Vent DNA polymerase in a Robocycler 40 (Stratagene, LaJolla, Calif.) under the following conditions: incubation for 2 minutes at 95° for one cycle; 1 minute at 95°, 1 minute at 55°, 1 min at 72° for 30 cycles; 5 minutes at 72° for 1 cycle. PRC products and the PDT expression vector were digested with the corresponding restriction endonucleases, purified from 1 percent low melting point agarose gel, in-gel ligated, and transfected in E. coli JM109. The positive recombinants (pDt-h$A_1$ and pDt-h$A_{2A}$) were purified with the Wizard megaprep DNA purification system and sequenced with receptor and vector specific primers. H/F-$A_{2A}$cDNA was transferred into pVL1392 baculovirus expression vector, using Eco RI/Bam HI resulting in pVL-H/F-h$A_{2A}$. To generate the plasmids that will express native receptors, the HIS$_6$-FLAG nucleotide sequences were excised using Xba I/Nru I for PDT-h$A_1$ and Eco RI/Xba I for pVL-H/F-$A_{2A}$. The resulting linear CDNAS were filled in with Klenow and religated.

Similar methods were employed for $A_{2b}$ and $A_3$ receptors.

EXPRESSION OF RECOMBINANT HUMAN $A_1$ AND $A_{2A}$ ADENOSINE RECEPTORS:

Native and H/F-$A_1$ adenosine receptors were introduced into CHO-K1 cells by means of lipofectin, and colonies were selected by growth of cells in 1 mg/mL G418. Transfected CHO-K1 cells were maintained in Ham's F12 medium with 10 percent fetal bovine serum, 100 U/mL penicillin, 100 µg/mL streptomycin, 2.5 µg/mL amphotericin B and 0.5 mg/mL G418. Since native and H/F-$A_{2A}$ adenosine receptors were poorly expressed in CHO-K1 cells, these were also expressed in Sf9 insect cells using the baculovirus transfer vector and linear AcMNPV wild-type viral DNA. Sf9 cells were grown in TNM-FH medium supplemental with 10 percent fetal bovine serum, 2.5 µg.ml amphotericin B and 50 µg/mL gentamicin and were harvested 45–65 hours post recombinant virus infection.

MEMBRANE PREPARATION:

CHO-K1 monolayers were washed with PBS and harvested in buffer A (10 mM HEPES), 10 mM EDTA, pH 7.4), supplemented with protease inhibitors (10 µg/mL benzamidine, 100 µM phenylmethylsulfonyl fluoride, and 2 µg/mL of each aprotinin, pepstatin, and leupeptin). The cells were homogenized in a Polytron (Brinkmann) for 20 seconds, then centrifuged at 30,000 g, and the pellets were washed twice with buffer HE (10 mM HEPES, 1 mM EDTA, pH 7.4, containing protease inhibitors). The final pellet was resuspended in buffer HE, supplemented with 10 percent sucrose, and frozen in aliquots at −80°. Sf9 cell suspensions were washed twice in insect PBS (6.8 mM $CaCl_2$, 55 mM KCl, 7.3 mM $NaH_2PO_4$ and 47 mM NaCl, pH 6.2) resuspended in buffer B (10 mM Tris, 25 mM NaCl, 10 mM $MgCl_2$, 1 mM EDTA, 1 µM adenosine, pH 7.4, containing protease inhibitors) burst by $N_2$ cavitation (600 psi, 20 minutes), and homogenized. The homogenate was centrifuged at 30,000 g for 30 minutes, and the pellet was washed twice in buffer HE and stored in 25 mM HEPES, 250 Mm NaCl, 10 percent glycerol with protease inhibitors at −80°. To determine protein concentrations, membranes purified receptors and bovine serum albumin standards were dissolved in 0.2 percent NaOH/0.01 percent SDS, and protein was determined using fluorescamine fluorescence as modified. Lindenetal, J. Biol. Chem. 259:15115–15122 (1984).

CYCLIC AMP ASSAYS:

CHO-K1 cells were incubated without or with 100 mg/mL pertussis toxin. The cells were removed from tissue culture plates upon the addition of PBS containing 5 mM EDTA, washed twice with PBS, and resuspended in serum-free (DMEM supplemented with 20 mM sodium-HEPES (H-DMEM) . Aliquots of cells (60,000/200 µL) were transferred to test tubes and maintained at 1 hour at ambient temperature. Fifty microliters of H-DMEM was added containing (final concentrations): 1 U/Ml adenosine deaminase±5µM forskolin and various amounts of CPA. The cells were transferred to a 37° Shaker bath and incubated for 10 minutes before being lysed by the addition of 0.5 mL of 0.15 N HCL and centrifuged at 1700 g for 10 minutes. Five-hundred microliters of the supernatants were removed, acetylated, and assayed for cyclic AMP by automated radioimmunoassay.

MEMBRANE PHOTOAFFINITY LABELING AND SDS-PAGE:

The $A_1$ adenosine receptor antagonist photoaffinity label $^{125}$I-Az-BW-A844, was prepared as described previously. Patel et al, "Mol. Pharmacol." 33:585–591 (1988). CHO-K1 membranes expressing human H/F-$A_1$ adenosine receptor were incubated for 1.5 hours at room temperature in dim light with $^{125}$I-Az-BW-A844U ($6 \times 10^7$ cpm) in the presence of 10 μM GTPγS. After the incubation period, the membranes were irradiated with UV light for 15 minutes, then centrifuged at 100,000 g for 30 minutes, and the pellet was resuspended in 1 mL of 2×buffer C (1×=25 mM HEPES, 150 mM nACl, pH 7.4, supplemented with protease inhibitors). Crude digitonin-solubilized or purified receptors were subjected to SDS 12 percent polyacrylamide gel electrophoresis. Samples were not heated prior to electrophoresis since this resulted in aggregation of purified receptors. SDS gels were dried and exposed to Hyperfilm ECL autoradiography film (Amersham, Arlington Heights, Ill.) with intensifying screens at −80° for 6–18 hours. In some cases, protein in SDS gels was stained with silver. The protein content of adenosine receptors in individual lanes of gels was estimated by densitometry (Molecular Dynamics Personal Densitometer) using ovalbumin standards and ImageQuant Software.

RECEPTOR SOLUBILIZATION:

One volume of 4 percent digitonin was added to an equal volume of H/F-$A_1$ adenosine receptor membranes (10 mg protein/mL) and incubated for 1 hour on ice with constant rocking. After centrifugation at 100,000 g for 30 minutes, the supernatant was used for receptor purification.

ANTI-FLAG AFFINITY CHROMATOGRAPHY:

Digitonin-solubilized human H/F-$A_1$ adenosine receptors were diluted with buffer C to a final digitonin concentration of 0.2 percent and loaded twice by gravity onto 1 mL anti-FLAG antibody columns prewashed with buffer C plus 0.2 percent digitonin (buffer CD). The column was washed with 3×12 mL buffer CD, and the receptor was eluted with 4×1 mL fractions of CD supplemented with 200 μg/mL FLAG peptide. Aliquots (40 μL) of the load, pass-through final wash and elution fractions were electrophoresed. Some samples were incubated with 0.5 U N-glycosidase F at 37° for 18 hours prior to electrophoresis. This enzyme was chosen based on its broad activity on all types of mammalian N-glycan chains.

Ni-NTA AFFINITY CHROMATOGRAPHY, COLUMN PROCEDURE:

Elution fractions (2 mL) from an anti-FLAG column were loaded by gravity onto 1 mL Ni-NTA-agarose columns prewashed with buffer CD plus 1 mM imidazole. Columns were washed four times with 1.5 ml of wash buffer and eluted with 5×1 mL of the same buffer supplemented with 200 mM imidazole, pH 7.4.

Ni-NTA AFFINITY CHROMATOGRAPHY, MICROFUGE TUBE PROCEDURE:

Elution fractions (500 μL) from anti-FLAG columns containing H/F-Al were added to microfuge tubes containing 250 μL Ni-NTA-agarose prewashed three times with buffer CD plus 1 mM imidazole. After incubating on a rocker for 40 minutes at 4°, the tubes were centrifuged at 5000 g for 10 minutes, and the supernatant was removed. The resin was washed twice with 800 μL of buffer CD plus 1 mM imidazole and eluted two times with 200 μL of buffer CD plus 200 mM imidazole.

RADIOLIGAND BINDING ASSAYS:

Saturation binding assays for human $A_1$ adenosine receptors were performed with the agonist $^{125}$I-ABA and the antagonist [$^3$H]CPX. [$^3$H]CGS21680 and [$^3$H]NECA were used as radioligands for binding to membranes made from Sf9 insect cells expressing $A_{2A}$ receptors. None of these ligands bound specifically to membranes prepared from cells lacking recombinant receptors. The experiments were performed in triplicate with 10 μg membrane protein in a total volume of 0.1 mL with 0.5 U/mL adenosine deaminase, with and without 5 mM $MgCl_2$ for agonist and antagonist binding, respectively. The incubation time was 3 hours for agonists and 2 hours for the antagonists at 21°. Nonspecific binding was measured in the presence of 1 μM CPX and 100 μM NECA for $A_1$ and $A_{2A}$ receptors, respectively. Competition experiments were carried out using 1 nM $^{125}$I-ABA for $A_1$ receptors and 70 nM [$^3$H]NECA for $A_{2A}$ receptors. $B_{max}$ and $K_D$ were calculated by nonlinear least squares interpolation for single or two-site binding models. $K_1$ values for different compounds were derived from IC50 values. Data from replicate experiments were tabulated as means ± SEM.

RESULTS:

Expression and Radioligand Binding Studies:

The extra amino acid sequence added to the amino termini of the $A_1$ and $A_{2A}$ adenosine receptors to make the corresponding H/F receptors is: Met-Ala- (His) $_6$-Asp-Tyr-Lys-Asp-Asp-Asp-Asp-Lys-Ser-Arg (SEQ ID NO:B). The Ala just prior to the hexahistidine is added to permit the inclusion of a Kozak sequence to enhance receptor expression. The two amino acids included after the FLAG peptide (Ser-Arg) result from expression of the Xba I restriction site used to subclone the receptor cDNAs into expression vectors. Thus, 18 amino acids are added to these receptors, including a new initiation Met, hexahistidine, the eight amino acid FLAG peptide, and three other amino acids. The modified receptors increase in molecular mass by 2.26 kDa.

Stable lines were established in CHO-K1 cells that express native- and H/F-$a_1$ adenosine receptors as well as $A_{2b}$ and $A_3$ adenosine receptors. It was confirmed that neither $A_1$ and $A_{2A}$ adenosine receptors are endogenously expressed in untransfected CHO-K1 cells. Screening of G418 selected colonies for [$^3$H]CPX binding identified clones for H/F-$A_1$ receptors ($B_{max}$=30.7±2.1 pmol/mg protein), and a clone expressing native-A, receptors (10±1.8 pmol/mg protein). The $K_D$ for [$^3$H]CPX is similar to the dissociation constant previously reported for $A_1$ adenosine receptors measured in human cerebral cortical membranes and transfected CHO cell membranes. The agonist radioligand $^{125}$I-ABA also bound with similar affinities to sites on native- and H/F-$A_1$ receptors. (FIG. 2) The number of $^{125}$I-ABA binding sites detected was lower than the number of [$^3$H]CPX binding sites, suggesting that only a subset of receptors was labeled by the agonist radioligand over the concentration range used.

$A_{2A}$ receptors were poorly expressed in transfected CHO cells (<0.2 pmol protein). Hence, native and H/F-$A_{2A}$ receptors were expressed in Sf9 cells. Similar amounts of receptors were detected using [$^3$H]CGS21680 and [$^3$H]NECA. $B_{max}$ values for native-and H/F-$A_{2A}$ receptors in Sf9 cell membranes were: 18.7±3.4 and 48±4.4 pmol/mg protein, respectively. Data from 30 equilibrium binding experiments using membranes from cells that express native- or H/F-$A_1$ and $A_{2A}$ adenosine receptors are summarized in Table 1 below. The H/F expression had no significant effect on the binding affinities any of the four radioligands tested. The H/F extension also did not impair expression of the recombinant receptors; in fact, the H/F receptors were expressed at 2–3 times higher levels than their corresponding native counterparts.

TABLE 1

SUMMARY OF RADIOLIGAND
BINDING PARAMETERS TO RECOMBINANT
HUMAN NATIVE- AND H/F-A$_1$ AND A$_2$ ADENOSINE RECEPTORS

| Radioligand | K$_D$ (nM) | B$_{max}$ (pmol/mg Protein) | N | KD (nM) | B$_{max}$ (pmol/mg Protein) | N |
|---|---|---|---|---|---|---|
| $^{125}$I-ABA (High Affinity Sizes) | 102 ± 0.03 | Native-A1 3.5 ± 0.8 Native-A$_1$ | 3 | 0.98 ± 0.16 | H/F-A$_1$ 3.3 ± 0.5 H/F-A$_1$ | 3 |
| [$^3$H]CPX | 2.38 ± 0.07 | 10.0 ± 1.8 Native-A$_{2A}$ | 3 | 2.80 ± 0.58 | 30.7 ± 2.1 H/F-A$_{2A}$ | 3 |
| [$^3$H]CGS-21680 | 125 ± 21 | 18.7 ± 3.4 Native-A$_{2A}$ | 5 | 179 ± 22 | 48.0 ± 4.4 H/F-A$_{2A}$ | 4 |
| [$^3$H]NECA | 125 ± 22 | 18.4 ± 2.2 | 5 | 160 ± 32 | 36 ± 5 | 4 |

ASSESSMENT OF RECOMBINANT RECEPTOR COUPLING TO G PROTEINS

Figure 3A:
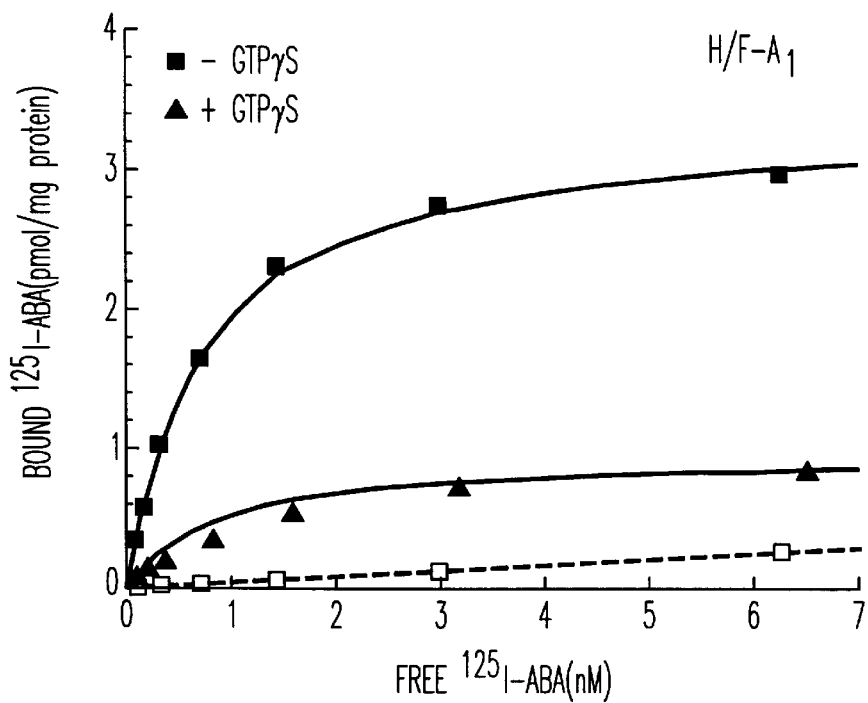
FIG. 3 demonstrates the effect of GTPγS on equilibrium binding of radioligands to human recombinant H/F-A$_1$ and H/F-A$_{2A}$ adenosine receptors.
Figure 3B:
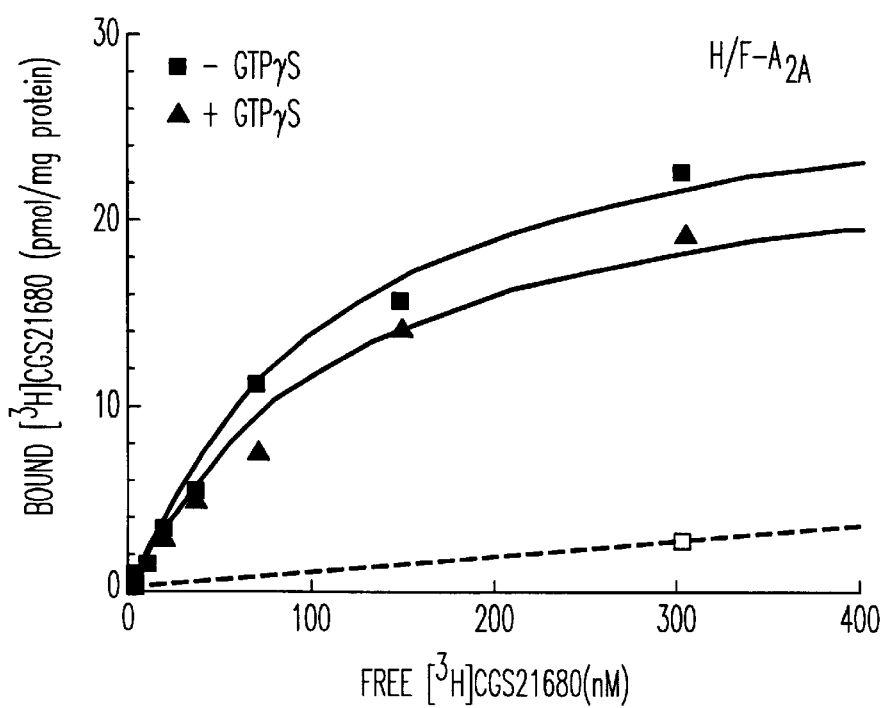

The binding of $^{125}$I-ABA to Al receptors may represent a subset of receptors coupled to G proteins. As was the case for native-A$_1$ receptors, the addition of GTPγS caused a large reduction in the number of high affinity agonist binding sites to H/F-A$_1$ receptors. (FIG. 3) The number of high affinity $^{125}$I-ABA binding sites was similar for the native and H/F-A$_1$ receptors, but the fraction of coupled receptors, calculated as the ratio of high affinity $^{125}$I-ABA binding sites to [$^3$H]CPX binding sites, was 35 percent for native-A$_1$ and 10 percent for H/F-A$_1$. While it is possible that the H/F extension contributes to this difference, it is believed that it is more likely that the number of coupled receptors is limited by the complement of G proteins in these cells, and a higher fraction of native receptors are coupled simply because fewer native receptors are expressed.

[$^3$H]CGS21680 and [$^3$H]NECA bind to low affinity (K$_D$>100 nM) sites on Sf9 cell membranes. Binding to native A$_{2A}$ receptors was reduced only slightly by the addition of GTPγS. A similar insensitivity to GTPγS was noted in the case of the H/F-A$_{2A}$ receptor. These data suggest that recombinant A2A receptors on Sf9 cell membranes are poorly coupled to G proteins. Despite the fact that [$^3$H]CGS21680 and [$^3$H]NECA are agonists, they appear to bind with sufficiently high affinity to detect uncoupled GTPγS-insensitive A$_{2A}$ receptors. This ability to detect uncoupled A$_{2A}$ receptors with agonist radioligands is consistent with the recent finding that [$^3$H]CGS21680 binds to both G protein coupled and uncoupled rat striatal A$_{2A}$ receptors with K$_D$ values of 3.9 and 51 nM, respectively.

Figure 4D:
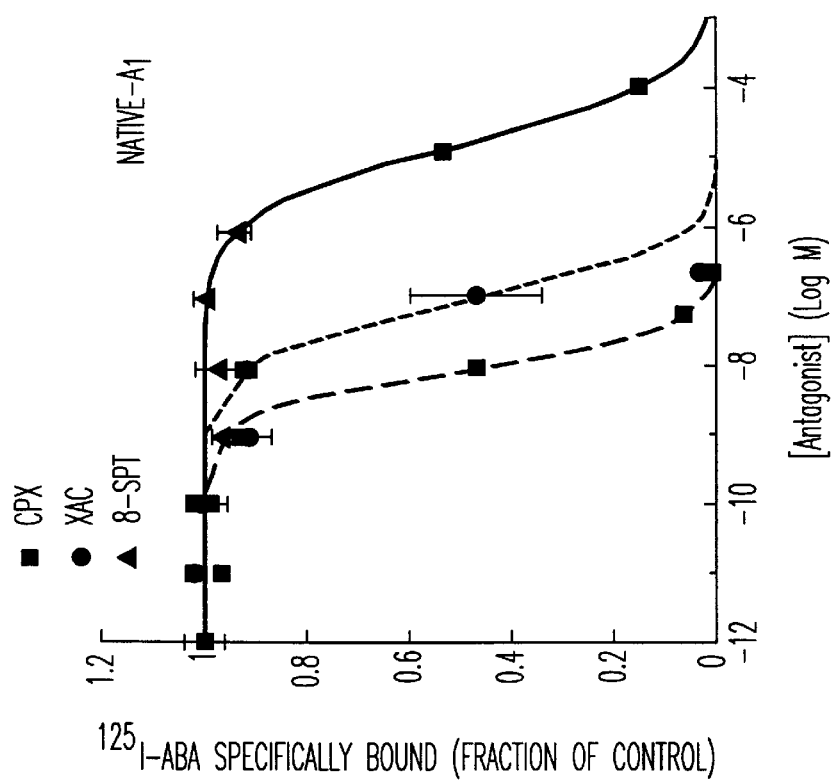
FIG. 4 is a graphic illustration of competition by various compounds for radioligand binding to recombinant human native and H/F-A$_1$ adenosine receptors.
Figure 4C:
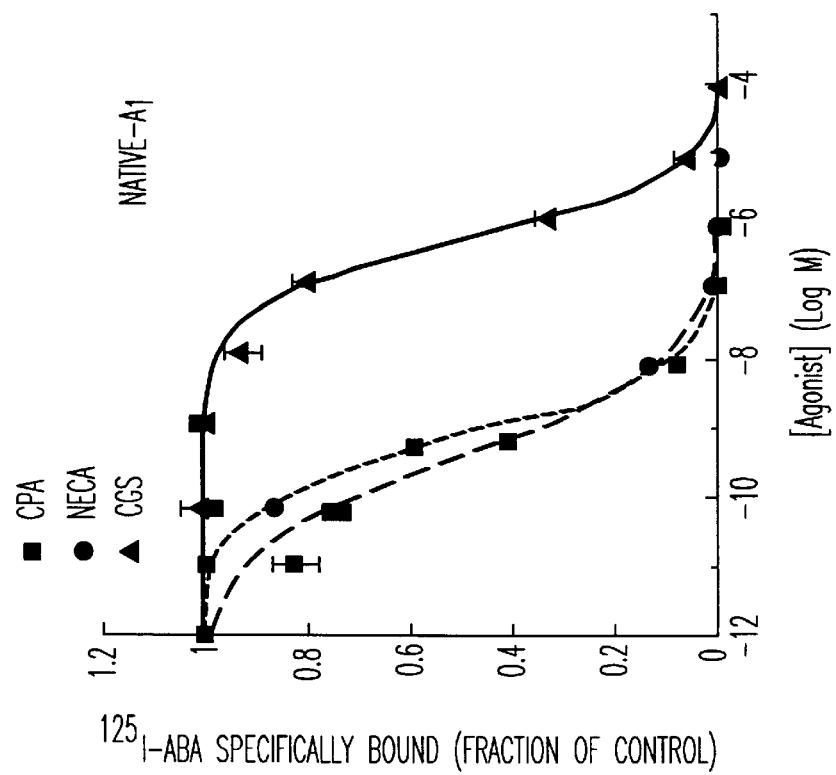

COMPETITIVE BINDING ASSAYS:

Twelve compounds were evaluated to determine their potencies to compete for radioligand binding to native- and H/F-A$_1$ or A$_{2A}$ receptors. The similarity between native- and H/F-A$_1$ receptors for six compounds is illustrated in FIG. 4. Data from 78 experiments are summarized in Table 2 below. There were no significant differences in K$_1$ values for native- and H/F-adenosine receptors among the competing compounds. On the average, the ratio of K$_1$ values (native: H/F) for A$_1$ receptors was 0.95±0.11 and for A$_{2A}$ receptors 0.81±0.07.

This is the first investigation in which the binding affinities of several compounds to recombinant human A$_{2A}$ receptors have been determined. The results, tabulated in Table 2 below, are in fairly good agreement with K$_1$ determinations based on competition for [$^3$H]CFS21680 binding to human striatal membranes. Ji et al, "J. Recept. Res.". 12:149–169 (1992). These earlier studies using striatal tissue were complicated by the coexistence of multiple adenosine receptor subtypes in the striatum and the existence of two agonist affinity sites of A$_{2A}$ receptors. Of particular note is the finding that CPX binds to recombinant human A$_1$ adenosine receptors with a K$_D$ of 2.4 nM, and K$_1$ 75 nM. Thus, this highly A$_1$ vs A$_{2A}$ selective compound in the rat (>400-fold) is only 31-fold selective for human receptors.

CYCLIC AMP ASSAYS:

The selective A$_1$ adenosine receptor agonist CPA had no effect on cyclic AMP levels in untransfected CHO-K$_1$ cells at concentrations up to 1 μM. In cells transfected with native-A$_1$ adenosine receptors, CPA potently (EC$_{50}$=0.37 nM) inhibited forskolin-stimulated cyclic AMP accumulation. (FIG. 5) The high potency of CPA may be due to the high density of recombinant receptors in these cells. CPA also potently inhibited cyclic AMP accumulation in cells transfected with H/F-A$_1$ adenosine receptors, and this effect was abolished in cells preincubated with pertussis toxin. The data suggests that the H/F extension of A$_1$ adenosine receptor does not modify the G protein coupling characteristics of the Al adenosine receptor.

TABLE 2

SUMMARY OF THE K$_1$ VALUES OF COMPOUNDS TO COMPETE
FOR RADIOLIGAND BINDING TO
RECOMBINANT HUMAN NATIVE- AND H/F RECEPTORS

| COMPETITOR | K$_1$ (nM) NATIVE-A$_1$ (N = 3) | NH | K1 (nM) H/F A$_1$ | NH | N |
|---|---|---|---|---|---|
| CPA | 0.34 ± 0.05 | 0.93 ± 0.16 | 0.31 ± 0.08 | 0.79 ± 0.02 | 3 |
| NECA | 0.76 ± 0.12 | 0.95 ± 0.09 | 1.27 ± 0.36 | 0.97 ± 0.06 | 5 |
| XAC | 52.7 ± 9.2 | 1.12 ± 0.11 | 50.6 ± 7.0 | 0.96 ± 0.08 | 5 |
| CGS21680 | 331 ± 22 | 0.92 ± 0.04 | 416 ± 130 | 0.95 ± 0.07 | 5 |
| 8-SPT | 7570 ± 1075 | 0.87 ± 0.05 | 6210 ± 2579 | 0.84 ± 0.06 | 3 |

| COMPETITOR | K$_1$ (nM) NATIVE-A$_{2A}$ (N = 3) | NH | K$_1$ (nM) H/F A$_{2A}$ (N = 3) | NH |
|---|---|---|---|---|
| XAC | 18.4 ± 1.5 | 1.13 ± 0.04 | 18.6 ± 1.9 | 1.11 ± 0.04 |
| 1ABOPX | 23.7 ± 7.5 | 0.84 ± 0.17 | 22 ± 3.6 | 0.94 ± 0.14 |
| CPX | 75 ± 14 | 0.80 ± 0.06 | 85 ± 7.2 | 0.77 ± 0.11 |

TABLE 2-continued

SUMMARY OF THE $K_1$ VALUES OF COMPOUNDS TO COMPETE FOR RADIOLIGAND BINDING TO RECOMBINANT HUMAN NATIVE- AND H/F RECEPTORS

| | | | | |
|---|---|---|---|---|
| NECA | 114 ± 41 | 0.90 ± 0.13 | 142 ± 49 | 0.87 ± 0.09 |
| CGS21680 | 132 ± 9.4 | 0.75 ± 0.06 | 197 ± 4.5 | 0.75 ± 0.01 |
| R-PAI | 928 ± 95 | 0.78 ± 0.05 | 1530 ± 104 | 0.77 ± 0.01 |
| I-ABA | 621 ± 48 | 1.0 ± 0.13 | 914 ± 99 | 0.89 ± 0.06 |

Competition experiments were carried out using 1 nM $^{125}$I-ABA for $A_1$ receptors and 70 nM [$^3$H]NECA for $A_{2A}$ receptors. $K_1$ values for receptors were determined as described under Materials and Methods. $K_1$ values for agonists (indicted in italics) reflect high and low affinity sites of $A_1$ and $A_{2A}$ receptors, respectively. N = Hill coefficient. Values are means ± SEM.

PURIFICATION OF H/F-$A_1$ RECEPTORS:

To test the efficiency of anti-FLAG antibody columns and Ni-NTA columns to retain H/F-modified adenosine receptors, human H/F-$A_1$ receptor was used as a prototype. Small batches of membranes made from CHO-$K_1$ cells expressing native and H/F-$A_1$ receptors were photoaffinity labeled with the $A_1$ selective antagonist $^{125}$I-Azido-BW-A844U. After digitonin treatment, the soluble fraction was loaded twice on an anti-FLAG affinity column. Following extensive washing, the receptor was eluted in four 1-mL fractions, each containing 200 μg of the FLAG peptide. The elution profile was monitored by counting a portion of each fraction and by autoradiography following SDS-PAGE. Digitonin was found to solubilize 50–60 percent of specific [$^3$H]CPX binding sites. No photoaffinity labeled native-$A_1$ receptors adhered to anti-FLAG columns, due presumably to the absence of the FLAG epitope. 80 percent of photoaffinity-labeled H/F-$A_1$ receptors adhered to the anti-FLAG column. Of the retained receptors, 65 percent were eluted with the FLAG peptide in fractions 1–2 and >90 percent in fractions 1–4. A broad major band was seen after gel electrophoresis of the load and the elution fractions with an apparent molecular mass of 38–43 kDa. After deglycosylation with N-glycosidase F, the labeled protein was quantitatively shifted to a molecular mass of 33–34 Kda. These findings are reasonably consistent with the deduced molecular mass of the H/F-$A_1$ receptor, 38.8 Kda, of which 2.26 kDa is derived from the H/F extension. The results also are in agreement with previous photoaffinity labeling experiments. Patel et al, supra. Application of crude digitonin-solubilized receptors to Ni-NTA columns resulted in poor retention (<25 percent) of the photoaffinity-labeled receptors. This is attributed to relatively low affinity of the Ni-NTA for the receptor, resulting in gradual elution of receptors during the loading of large volumes (>4 column volumes) of receptors to the Ni-NTA column. Ni-NTA was much more efficient when used as a second affinity column step with concentrated receptors.

To purify enough receptors to visualize on silver-stained SDS polyacrylamide gels, 84 mg of membranes derived from CHO-$K_1$ cells that stably express 20 pmol/mg protein H/F-$A_1$ receptors were purified as described above using anti-FLAG affinity columns, either alone or in combination with Ni-NTA. Most of the silver-strained protein eluted from the affinity columns ran as a diffuse silver-stained band at 38–43 kDa and shifted in molecular mass to 33–34 kDa upon treatment with N-glycosidase F. It is noted that the molecular mass of the deglycosylated H/F-$A_1$ adenosine receptor coincidentally corresponds to the molecular mass of N-glycosidase, but the receptor accounts for over 90 percent of the silver-stained protein. These molecular masses of the receptor before and after deglycosylation corresponded closely to the molecular masses of the photoaffinity-labeled receptors. A comparison was made between H/F-$A_1$ receptors purified by anti-FLAG columns alone with receptors purified by sequential anti-FLAG and Ni-NTA chromatography steps. The most noticeable difference between receptors purified by anti-FLAG chromatography alone and those purified by sequential chromatography was the removal of a 42 kDa peptide. The low abundance of silver-stained non-receptor proteins indicates that the receptor has been purified to near homogeneity. The total protein eluted from the anti-FLAG column, 106 μg (based on fluorescamine fluorescence), was reduced to 60 μg following Ni-NTA chromatography. This was derived from 65 μg receptor protein in the starting CHO cell membranes, as estimated from the number of [$^3$H]CPX binding sites. It is possible that the cells contain some receptors that are not capable of binding radioligand. As a means of estimating receptor protein on the silver-stained gel, the optical density of silver-stained receptors and ovalbumin standards was determined. By this analysis, over 100 μg of receptor protein was purified. This exceeds our estimates of the total protein in the sample based on fluorescamine fluorescence. However, since the silver staining of proteins in gels is variable, it is possible that silver stains the $A_1$ adenosine receptors more efficiently than ovalbumin. Based on densitometry of gel lanes, the receptor purified by sequential affinity chromatography steps appeared to be >90 percent pure.

Ni-NTA chromatography of receptors previously purified using anti-FLAG columns was useful to achieve somewhat higher purification. However, when loaded onto Ni-NTA columns, it was necessary to keep load and wash volumes small (<4 column volumes) to prevent leaching of H/F receptor off the Ni-NTA resin. An efficient microfuge tube procedure was developed as follows: Receptors eluted from an anti-FLAG column (1 mL) were mixed with 0.5 mL Ni-NTA resin, washed two times with 0.8 mL wash buffer, and eluted by twice adding 200 μL buffer plus 200 mM imidazole (see Materials and Methods). By this procedure, the recovery of photolabeled H/F-$A_1$ adenosine receptor was >80 percent.

Figure 6D:
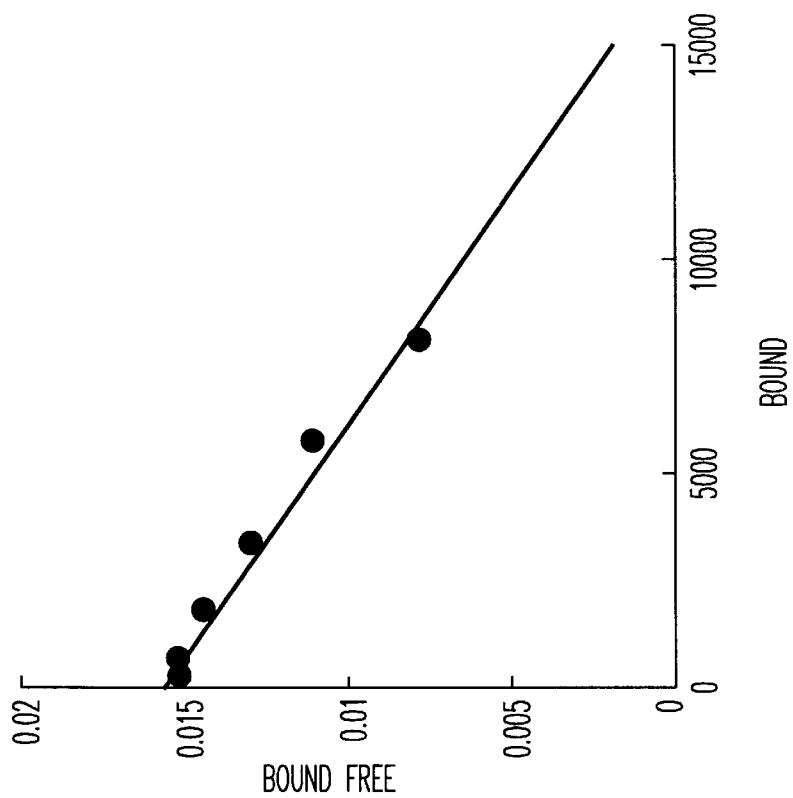
FIG. 6 demonstrates equilibrium binding of radioligands to recombinant human adenosine receptors as indicated.
Figure 6C:
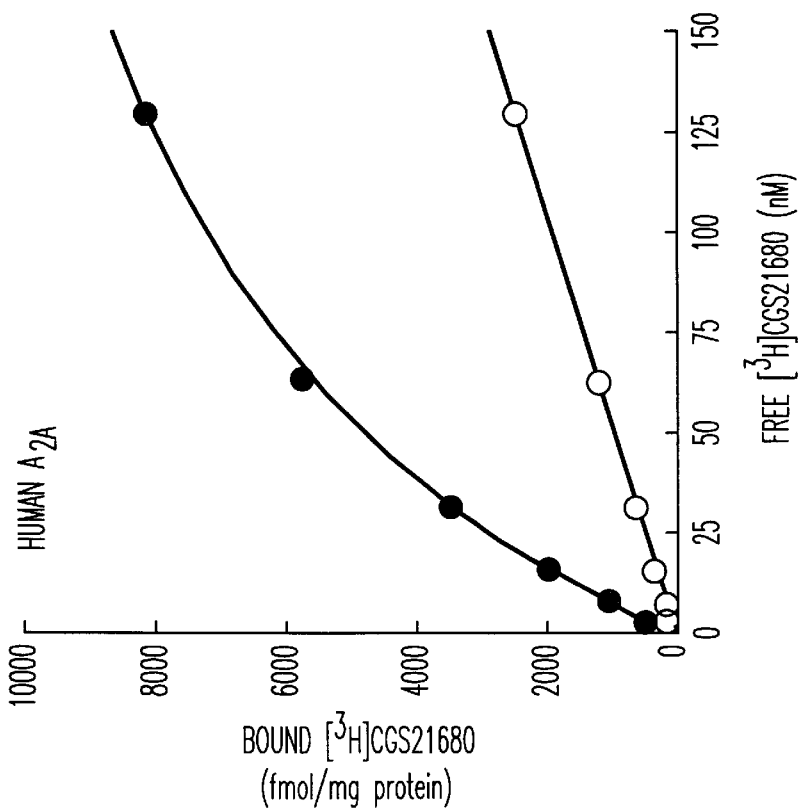
Figures 6E, 6F:
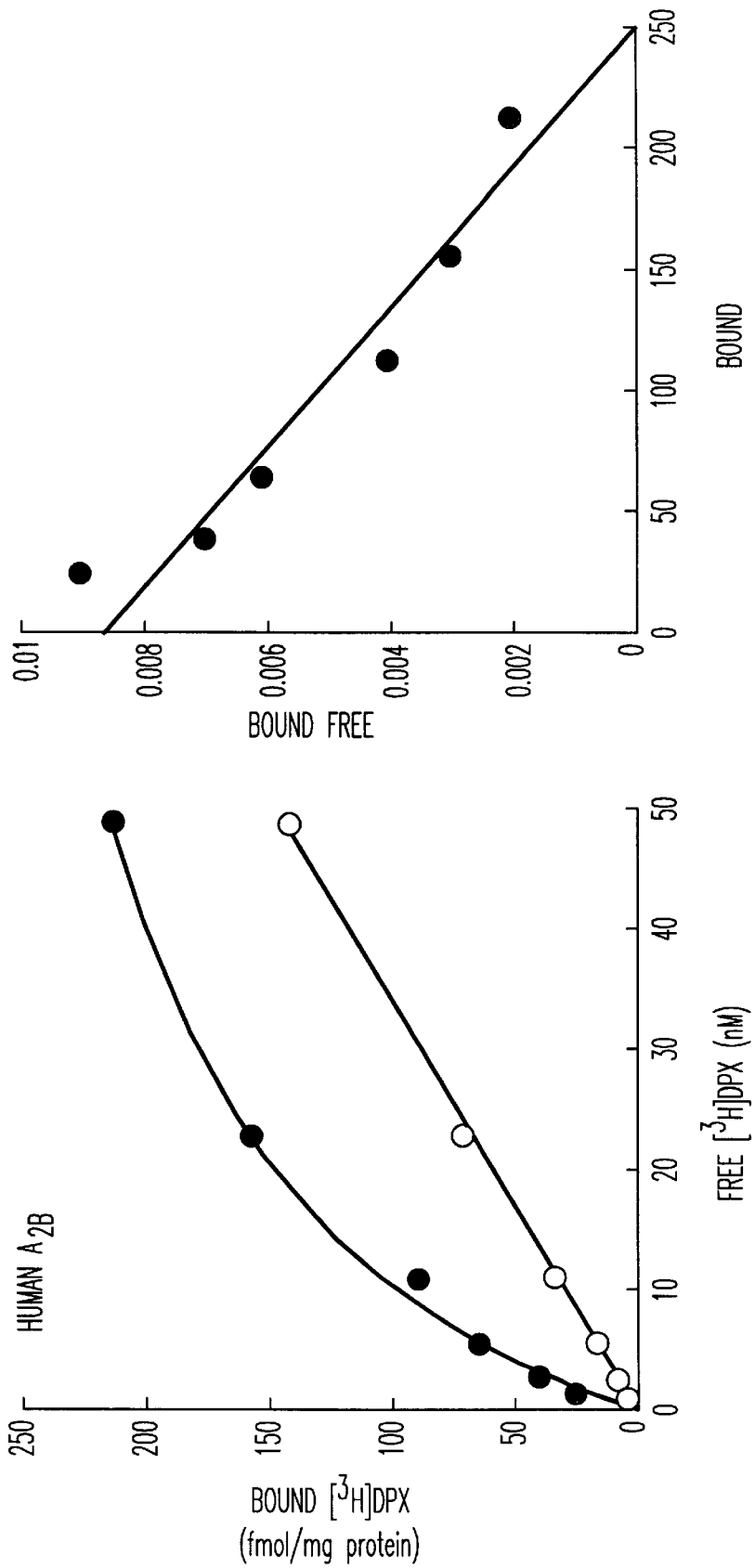

The radioligands used to label the $A_1$ and $A_{2A}$ receptors are commonly used and are commercially available. However, there are no reports in the literature of radioligands useful for detecting $A_{2B}$ receptors. In order to identify a potent antagonist we screened compounds based on their ability to inhibit cyclic AMP accumulation in $A_{2B}$ transfected HEK-293 cells stimulated by the agonist, NECA. 1,3-diethyl-8-phenylxanthine (DPX) was identified as a potent (p$A_2$=30 nM) antagonist as determined by Schild analysis. Based on this observation [$^3$H]DPX was custom triiated by NEN. The $A_{2B}$ binding assays shown in FIG. 6 demonstrate the first successful detection of $A_{2B}$ adenosine receptors by radioligand binding.

Applicants are the first to characterize the pharmacological properties of sheep and human $A_3$ adenosine receptors, and showed that they differ markedly from the previously cloned rat $A_3$ receptors. These receptors can be labeled nonselectively by agonist radioligands that also label $A_1$AR. Applicants have recently synthesized a novel antagonist radioligand $^{125}$I-ABOPX, the first $A_3$AR-selective radioligand.

Applicants screened commonly used agonist and antagonist compounds to determine their selectivities based on all four adenosine receptor subtypes. These include CPX and N-0861, $A_1$ selective antagonists, CGS21680, an $A_{2A}$ selective agonist and IB-MECA, and $A_3$ selective agonist. By this type of analysis, it has been found that CPX is only about 20-fold selective for $A_1$ vs. $A_{2B}$ receptors ($K_d$=2 and 40 nM, respectively), and >μM levels of CGS21680 activate $A_3$AR.

This information is useful for preventing misinterpretations about which receptors subtypes mediate various responses.

This invention finds utility in attempts to investigate adenosine receptor subtypes of xanthines that are used therapeutically. These include theophyline and enprofylline, to treat asthma. Although the $A_3AR$ transcript is abundant in human lung and the inhalation of adenosine by asthmatics causes mast cell degranulation and bronchoconstriction, theophylline was found to have very low affinity for rat and sheep A3AR, indicating that theophylline does not potently block $A_3AR$ in these species. However, when we examined the potency of theophylline to inhibit radioligand binding to human $A_3AR$ is 20 $\mu$M, well within the therapeutic range of theophylline or (10–50 $\mu$M). This underscores the importance of considering species differences and suggests that in some instances animal models may be inappropriate for screening compounds for activity on human receptors.

Selective compounds are useful for characterizing tissue receptor subtypes and identifying receptors that mediate physiological responses. For example, since we have discovered that $^{125}$I-ABA($A_1A_3$ nonselective) binding to lung membranes is not blocked by 1 $\mu$M of the $A_1$ selective antagonist WRC-0571, we have shown that the binding is blocked by the $A_3$-selective agonist IB-MECA. We have used lung homogenates from guinea pig and hamster to characterize $A_3$ receptors of these species and to draw conclusions about $A_3$-,mediated physiological responses in these species.

In order to understand the physiological effects mediated by a particular receptor subtype it is helpful to identify selective agonists and antagonists. The assignment of selectivity of adenosine receptors has usually been confined to a comparison of ligand binding to $A_1$ and $A_{2A}$ receptors in membranes derived from rat brain structures such as cortex and striatum, respectively. $A_{2B}$ receptors have been largely ignored due to the absence of use radioligands, and $A_3$ receptors were not identified until recently. An additional complication is the existence of marked species differences in ligand binding, particularly to $A_3$ receptors. Attempts to extrapolate across species creates uncertainties in experimental interpretation. Many of these problems can be overcome by producing overexpressed recombinant receptors and developing improved radioligands.

The invention of this application has been described both generically, and with reference to specific examples. The examples are not intended to be limiting, and should not be so construed, save where specifically so indicated. In particular, altered sequences, concentrations, reactants and counting methods can be employed by those of ordinary skill in the art without the exercise of inventive faculty. Such alternatives remain within the scope of the invention, as defined by the claims set forth below.

---

What is claimed is:

1. A method of detecting binding of [$^3$H]1,3-diethyl-8-phenyl-xanthine to a human $A_{2B}$ adenosine receptor, comprising contacting said receptor, which is present in an amount of at least about 5 pmol/mg of protein, with said [$^3$H]1,3-diethyl-8-phenyl-xanthine under conditions which permit binding of said [$^3$H]1,3-diethyl-8-phenyl-xanthine to said $A_{2B}$ adenosine receptor to occur, washing said adenosine receptor to remove any unbound material, and inspecting the resulting sample to determine the presence of said [$^3$H]1,3-diethyl-8-phenyl-xanthine, wherein the presence and amount of said [$^3$H]1,3-diethyl8-phenyl-xanthine correlates with the presence and amount of binding of said [3H]1,3 -diethyl-8-phenyl-xanthine to said $A_{2B}$ adenosine receptor.

2. The method of claim 1, wherein said $A_{2B}$ adenosine receptor comprises the amino acid sequence for corresponding native $A_{2B}$ adenosine receptor, and further comprises recombinantly added marker groups of hexahistidine and the FLAG amino acid sequence Asp-Tyr-Lys-Asp-Asp-Asp-Asp-Lys (SEQ ID NO:1).

3. The method of claim 1, wherein the presence and amount of binding of said [$^3$H]1,3-diethyl-8-phenyl-xanthine is compared with an amount of binding of a target compound with said $A_{2B}$ adenosine receptor, and wherein said comparison is indicative of the effectiveness of said target compound as an $A_{2B}$ adenosine receptor antagonist or agonist.

4. The method of claim 3, wherein the method of detecting binding is a competitive binding assay.

5. The method of claim 3, wherein said target compound is a potentially therapeutically active compound.

6. A method of detecting binding of [$^3$H]1,3-diethyl-8-phenyl-xanthine to a human $A_{2B}$ adenosine receptor, comprising contacting a membrane with said [$^3$H]1,3-diethyl-8-phenyl-xanthine, wherein said membrane is comprised of a plurality of said $A_{2B}$ adenosine receptors which are present in an amount of at least about 5 pmol/mg of protein, under conditions which permit binding of said [$^3$H]1,3-diethyl-8-phenyl-xanthine to said $A_{2B}$ adenosine receptors to occur, and detecting binding of said [$^3$H]1,3-diethyl-8-phenyl-xanthine to said $A_{2B}$ adenosine receptors.

7. The method of claim 6, wherein said $A_{2B}$ adenosine receptors comprise the amino acid sequence for corresponding native $A_{2B}$ adenosine receptor, and further comprise recombinantly added marker groups of hexahistidine and the FLAG amino acid sequence Asp-Tyr-Lys-Asp-Asp-Asp-Asp-Lys (SEQ ID NO:1).

* * * * *

UNITED STATES PATENT AND TRADEMARK OFFICE
CERTIFICATE OF CORRECTION

PATENT NO. : 5,854,081
DATED : December 29, 1998
INVENTOR(S) : Joel LINDEN, et al.

It is certified that error appears in the above-identified patent and that said Letters Patent is hereby corrected as shown below:

On the title page, item [73] should be:

--[73] Assignee: The University of Virginia Patent Foundation, Charlottesville, VA--.

Signed and Sealed this

Third Day of August, 1999

Attest:

Q. TODD DICKINSON

*Attesting Officer*    *Acting Commissioner of Patents and Trademarks*